United States Patent
McVey

(10) Patent No.: US 7,157,045 B2
(45) Date of Patent: *Jan. 2, 2007

(54) INFRARED MONITOR AND CONTROL FOR VAPOR HYDROGEN PEROXIDE PROCESSING TECHNIQUES

(75) Inventor: Iain F. McVey, Lakewood, OH (US)

(73) Assignee: Steris Inc., Temecula, CA (US)

( * ) Notice: Subject to any disclaimer, the term of this patent is extended or adjusted under 35 U.S.C. 154(b) by 712 days.

This patent is subject to a terminal disclaimer.

(21) Appl. No.: 10/191,821

(22) Filed: Jul. 9, 2002

(65) Prior Publication Data

US 2003/0021724 A1 Jan. 30, 2003

Related U.S. Application Data

(60) Provisional application No. 60/304,367, filed on Jul. 10, 2001.

(51) Int. Cl.
*A61L 2/24* (2006.01)
(52) U.S. Cl. ............... 422/3; 250/339.13; 250/343; 422/4; 422/28; 422/105
(58) Field of Classification Search ............. 422/62, 422/3, 4, 28, 105; 250/339.12, 339.13, 343
See application file for complete search history.

(56) References Cited

U.S. PATENT DOCUMENTS 5,445,792 A * 8/1995 Rickloff et al. ............... 422/28
5,847,393 A 12/1998 Van Den Berg et al. .................. 250/339.13
5,872,359 A 2/1999 Stewart et al. ......... 250/339.12
5,886,348 A 3/1999 Lessure et al. ........ 250/339.13
5,892,229 A 4/1999 Crozier et al. ......... 250/339.13
6,542,762 B1 * 4/2003 Alam et al. .................. 600/310
6,875,399 B1 * 4/2005 McVey ........................... 422/3

FOREIGN PATENT DOCUMENTS

EP 384 535 8/1990
GB 1104636 2/1968

* cited by examiner

Primary Examiner—Krisanne Jastrzab
(74) Attorney, Agent, or Firm—Fay, Sharpe, Fagan, Minnich & McKee, LLP

(57) ABSTRACT

A vaporizer (14) supplies hydrogen peroxide and water vapor to a high level disinfection or sterilization region (20). Mid-infrared light detectors (32) detect light in the mid-infrared range which has traversed a region of the treatment chamber in a first narrow spectrum centered at 8,000 nanometers which is absorbed by the hydrogen peroxide vapor, a second narrow spectrum which is absorbed by the water vapor, and a third spectrum that is absorbed by neither the hydrogen peroxide vapor nor the water vapor. From these measurements, an absorbance or transmittance is determined (40) from which the concentrations of hydrogen peroxide and water vapor are determined (42). Monitored temperature (44) and the determined concentrations are converted into a percent saturation (54). The supply of hydrogen peroxide and water vapor to the chamber is controlled (60) in accordance with the determined percent saturation.

28 Claims, 1 Drawing Sheet

INFRARED MONITOR AND CONTROL FOR VAPOR HYDROGEN PEROXIDE PROCESSING TECHNIQUES

This application claims the benefit of U.S. Provisional Application Ser. No. 60/304,367, filed Jul. 10, 2001.

BACKGROUND OF THE INVENTION

The present invention relates to the vapor hydrogen peroxide arts. It finds particular application in the sensing of vapor hydrogen peroxide concentrations, as well as in the control of vapor hydrogen peroxide sterilization and other processing systems.

Typically, hydrogen peroxide vapor sterilization systems include a heater for vaporizing an aqueous hydrogen peroxide solution. The hydrogen peroxide and water vapor are carried in and through a sterilization or other treatment chamber. In the chamber, the hydrogen peroxide vapor kills microorganisms in an oxidizing reaction which converts the hydrogen peroxide vapor into water vapor. The water vapor and remaining hydrogen peroxide vapor are typically exhausted from the chamber. Because hydrogen peroxide breaks down quickly in sunlight, the vapor can be discharged to the atmosphere. Alternately, the hydrogen peroxide vapor can be converted into water vapor and the carrier air dried and recirculated to the vaporizer in a closed loop.

Typically, the aqueous hydrogen peroxide is fed to the vaporizer at a rate intended to maintain a preselected minimum hydrogen peroxide concentration in the chamber, but not so fast that the vapor in the chamber becomes saturated. Condensation will deplete the concentration of the hydrogen peroxide in the vapor (the condensate being greatly enriched in hydrogen peroxide), reducing the overall efficacy of the process. The condensate (being concentrated hydrogen peroxide) may also cause significant material compatibility issues. However, other than setting cycle parameters to avoid oversaturation of the vapor, the saturation of the process has not typically been monitored or controlled. The temperature in the chamber is typically held at a preselected temperature that is selected in accordance with the temperature compatibility of the products being sterilized in the chamber. The selected temperature is selected sufficiently high that the hydrogen peroxide vapor reacts effectively with microorganisms, but not so high that the hydrogen peroxide breaks down into oxygen and water vapor at too high a rate to maintain the selected hydrogen peroxide concentration in the chamber.

Various techniques have been proposed for monitoring hydrogen peroxide vapor concentration. These include electrochemical methods such as catalytic gates, amperometric measurements, and potentiometric measurements. However, electrochemical measurement techniques have various drawbacks. Typically, they rely on mass transfer across a gas/liquid or gas/solid interface. This results in longer time constants and a slow response of the control system. The output of electrochemical sensors is sensitive to the amount of gas movement proximate to the sensor. Electrochemical methods are not species specific. Interfering species cannot typically be separated. Calibration of electrochemical sensors is complex and typically requires return of the sensor to the manufacturer for factory calibration. Further, electrochemical techniques are temperature and pressure sensitive. The need for temperature compensation complicates calibration. When the sterilization chamber is held in the vacuum range, the vacuum significantly complicates and can even defeat concentration measurements with electrochemical methods. Electrochemical sensors typically do not measure the concentration of water vapor requiring use of a humidity sensor if saturation is to be determined.

Concentrations of water and hydrogen peroxide vapor can also be determined with spectroscopic methods. Hydrogen peroxide and water vapor both have a multiplicity of spectral lines at characteristic frequencies. In the infrared ranges, the spectral lines are so dense that they are generally viewed as a continuum, hydrogen peroxide and water vapor each having a characteristic curve or frequency absorption spectrum.

Hydrogen peroxide has a spectrum in the ultraviolet range. Ultraviolet light is not strongly absorbed by hydrogen peroxide, hence a weak signal is provided. Also, ultraviolet light degrades hydrogen peroxide breaking it down into water vapor and oxygen. Further, although hydrogen peroxide concentrations can be measured with ultraviolet light, there is typically no measurement of water vapor concentration. Without measuring the water vapor, the percent saturation cannot be determined.

Hydrogen peroxide and water vapor both have spectral peaks in the near infrared range. Although there may be spectral lines that are unique to water vapor or hydrogen peroxide vapor, the lines are closer together than the spectral differentiation of commonly available infrared sensors. When viewed as peaks or continuums, the hydrogen peroxide and water vapor peaks overlap significantly. Relatively complex calculations are needed to determination the concentrations of hydrogen peroxide and water vapor, individually, from the partially overlapping peaks. Moreover, there is a relatively weak energy transfer in the near infrared range. Thus, the output signals tend to be relatively weak. To eliminate noise problems in the weak signals, relatively expensive, more noise-free hardware is commonly utilized. Further, to improve the signal-to-noise ratio, a relatively long path length for the near infrared light through the vapor is utilized, often on the order of about 25 cm.

Prior techniques for controlling hydrogen peroxide vapor concentration have lacked sufficient credibility to be used alone to show that sterilization or high level disinfection in the chamber has been achieved. Rather, chemical indicators or biological indicators are commonly placed in the chamber. Chemical indicators undergo a color or other physical change in response to contact with peroxide vapor over time. However, because the chemical indicators typically only measure hydrogen peroxide concentration integrated over time, they are again only an indicator that sterilization or high level disinfection has been achieved and not considered proof. To prove that sterilization or disinfection has been achieved, biological indicators are typically utilized. Test spores in the biological indicators are exposed to the vapor in the chamber. The spores are then incubated for several days to see if any grow. Although highly reliable, biological indicators take several days to read. Typically, the sterilized goods are held in inventory for several extra days after sterilization until the biological indicator tests results are returned.

The present invention overcomes the above-referenced problems and others.

SUMMARY OF THE INVENTION

In accordance with one aspect of the present invention, a peroxy vapor system includes a light source which supplies light with at least a component in the mid-infrared range. A detector individually detects mid-infrared light in (a) a first narrow spectrum absorbed by peroxy vapor, (b) a second narrow spectrum absorbed by a carrier vapor, and (c) a third spectrum absorbed by neither the peroxy vapor nor the carrier vapor. A processor determines at least a concentration of the peroxy vapor from the detected light in the mid-infrared range.

In accordance with another aspect of the present invention, a peroxy vapor method is provided in which light in a mid-infrared range is projected through a monitored region. Mid-infrared light is detected in (a) a first narrow spectrum absorbed by the peroxy vapor, (b) a second narrow spectrum absorbed by a carrier vapor, and (c) a third spectrum absorbed by neither the peroxy nor the carrier vapor. At least a concentration of the peroxy vapor is determined from the light detected in the mid-infrared range.

In accordance with another aspect of the present invention, a high level disinfection or sterilization system is provided. A vaporizer vaporizes an aqueous peroxy solution from a solution source to form a peroxy vapor and a water vapor. The vaporizer supplies the peroxy and water vapors to a treatment chamber. A light source projects a beam of light in a mid-infrared range through the peroxy and water vapors. A mid-infrared light detector detects a first narrow spectrum absorbed by the peroxy vapor but not by the water vapor, a second narrow spectrum absorbed by the water vapor but not by the peroxy vapor, and a third spectrum absorbed by neither the peroxy nor the water vapor. An absorbance/transmittance processor converts the detected first, second, and third spectrum light into one of absorbance values indicative of mid-infrared light absorbed by the peroxy and water vapors and transmittance values indicative of mid-infrared light transmitted through the peroxy and water vapors. A processor converts the determined absorbance/transmittance values into a concentration of the peroxy vapor and a concentration of the water vapor. A temperature monitor monitors temperature in the treatment chamber. A percent saturation processor converts the concentration of peroxy vapor, the concentration of water vapor, and the temperature into an indication of a percent saturation in the treatment chamber. A control processor controls the generation of peroxy and water vapor in accordance with the determined percent saturation.

One advantage of the present invention resides in reduced component costs.

Another advantage of the present invention resides in compact probes.

Another advantage resides in more accurate control of sterilization or disinfection parameters.

Another advantage resides in greater control and monitoring of kill rates or D-values.

Another advantage of the present invention is that monitoring both concentration and percent saturation greatly improves the predictability that sterilization or high level disinfection has been achieved.

Still further advantages and benefits of the present invention will become, apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not be construed as limiting the invention.

DETAILED DESCRIPTION OF THE PREFERRED EMBODIMENT

Figure 1:
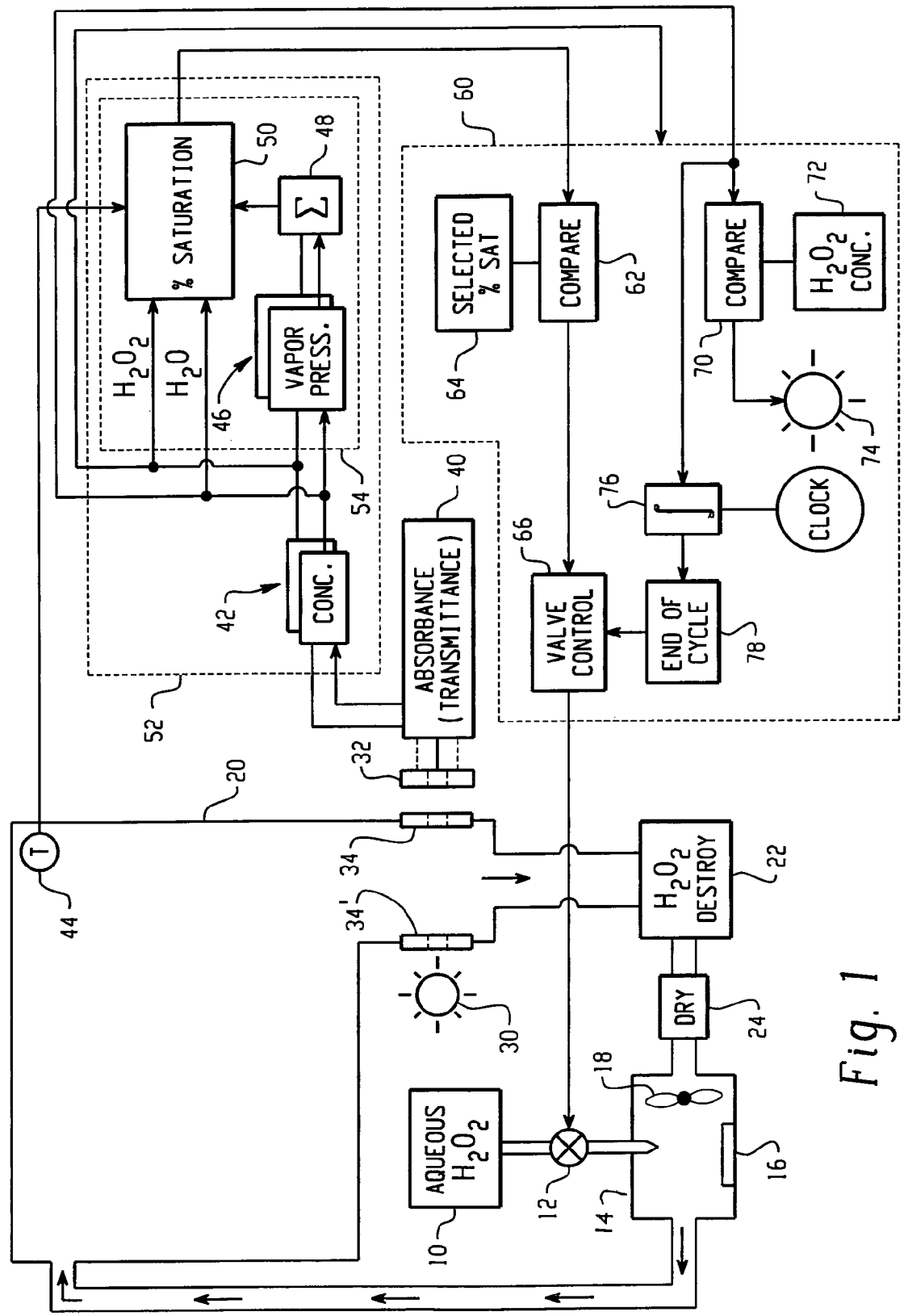
FIG. 1 is a diagrammatic illustration of a sterilization or high level disinfection system in accordance with the present invention.

Aqueous hydrogen peroxide, such as 35% or 50% solution is fed from a reservoir 10 through a control valve 12 into a vaporizer 14. In the vaporizer, the aqueous hydrogen peroxide is heated, such as with a heated plate 16. A fan or other blower mechanism 18 propels the vaporized hydrogen peroxide and water into a treatment chamber 20. The treatment chamber 20 may be relatively small for performing sterilization or high level disinfection on small items or may be relatively large, e.g., the size of a room, for treating pallets of completed product or other large quantities of material. At one or more points of the chamber, the vapor is exhausted from the chamber. The vapor from the chamber may be discharged to the atmosphere through a ventilation system. Alternately, the gas is fed to a hydrogen peroxide destroyer 22 which breaks down the hydrogen peroxide into water vapor. A dryer 24 removes the water vapor and passes dry gas to the fan 18 and the vaporizer 14. In some applications, all or a fraction of the exhausted vapor can be recirculated without being destroyed or removed.

A concentration sensor includes an illumination source 30, preferably an illumination source that generates light in the mid-infrared range, i.e., about 2200–15,000 nanometers (2.2–15 microns). The light source shines the infrared light through a portion of the chamber 20 and strikes one or more infrared detectors 32. A filter 34 is disposed between the illumination source and the detector to control the specific spectrum of light received by the detector. In the illustrated embodiment, the filter is adjacent the detector. Optionally, a filter 34' can be placed adjacent the illumination source either in addition to or instead of the filter 34. When a single detector 32 is provided, the filter 34 includes three filter regions which are moved progressively in front of the detector so that the detector receives mid-infrared light in each of three spectral ranges. The first narrow spectral range, preferably centered on 8,000 nanometers (8 microns) is a spectral range which is absorbed by hydrogen peroxide but not water vapor. One of the several spectral ranges or peaks in the mid-infrared range which are absorbed by water and not by hydrogen peroxide are passed by a second filter segment to the detector. Finally, the filter includes a filter segment which passes light in a spectral range which is not absorbed by either hydrogen peroxide or water vapor and which is near the selected hydrogen peroxide and water vapor spectral ranges to provide a background intensity. Rather than moving each of three filter segments in front of a single detector or illumination source, three stationary filter segments can be provided along with three detectors. Although the term "filter" is utilized, it is to be appreciated that there are various ways to separate out a relatively narrow frequency spectrum from a polychromatic light beam, such as by refraction. All such spectral range separation techniques are herein called "filtering" for simplicity of explanation.

However obtained, the intensity of light in the spectral range absorbed by hydrogen peroxide, the intensity of light in the range absorbed by water vapor, and the intensity of light in the background spectral range are communicated to a processor or other means 40 for calculating the absorbance or transmittance in each of the hydrogen peroxide and water vapor range. Transmittance is the log ratio of the intensity of transmitted light in the hydrogen peroxide or water vapor spectral range to the intensity of light in the background range. Absorbance is the converse of transmittance, i.e., it is the log ratio of the intensity of the absorbed light in the hydrogen peroxide or water vapor spectral range to the absorbed intensity in the background range. A concentration determining processor or means 42 is preprogrammed in accordance with the conventional tables for absorbance (transmittance) versus concentration. This relationship is typically described by a non-linear curve. The absorbance can be converted into concentration by solving a polynomial or other non-linear equation which describes the curve. However, because the present system is working in a relatively limited range of the curve, it is computationally faster and preferred to use a first look-up table which converts the absorbance or transmittance of hydrogen peroxide to its concentration and a second look-up table which converts the absorbance or transmittance of water vapor to concentration. Values falling between look-up table values can be determined by linear interpolation.

Once the concentration of hydrogen peroxide and water vapor are known and the temperature in the chamber is known, the partial pressure of each can be determined from commonly available tables. To this end, a temperature monitor 44 is positioned in the chamber to determine the temperature. There is again a non-linear relationship between the partial pressure relative to the concentration and temperature variables which can be described by a non-linear equation. However, it is again preferred to use look-up tables 46 which are addressed by the determined concentration of each of the hydrogen peroxide and water vapor and the monitored temperature to determine the corresponding partial pressure. A summing circuit 48 sums the two partial pressures which, because these are the only two components of vapor in the chamber, produces the vapor pressure in the chamber. When additional components are optionally added to the aqueous hydrogen peroxide, such as alcohol, the same procedure is followed to determine its contribution to the vapor pressure. The percent saturation is a known function of the concentration of the components, the pressure, and temperature. Again, a look-up table 50 is preferably provided which is addressed by the peroxide and water vapor concentrations, the vapor pressure, and the temperature to retrieve the corresponding percent saturation. Optionally, instead of using a plurality of look-up tables 42, 46, 50 addressing each other, a single large look-up table 52 can optionally be provided to convert the absorbance or transmittance of the hydrogen peroxide and water vapor and the chamber temperature directly into percent saturation. As yet another alternative, the saturation and vapor pressure look-up tables can be combined into a single look-up table 54 to provide a means which converts the hydrogen peroxide and water vapor concentrations and temperature directly into percent saturation.

The concentration of hydrogen peroxide vapor, the concentration of water vapor, the temperature, and the percent saturation are conveyed to a controller 60. In the illustrated embodiment, a saturation comparitor or means 62 compares the actually measured percent saturation with a preselected percent saturation 64, preferably just below 100%, e.g., 95–99%. The exact controlled percent will vary with the stability of conditions across the chamber 20. The set point percent saturation is selected to keep all areas, even the worse case region, below saturation conditions. When the measured percent saturation is below the selected percent saturation, the first comparitor 62 causes a valve controller 66 to open the aqueous hydrogen peroxide solution control valve 12. In this manner, the percent saturation is maintained substantially at the selected percent saturation.

A second comparitor or means 70 compares the measured hydrogen peroxide concentration with a preselected hydrogen peroxide concentration 72. In response to the measured hydrogen peroxide concentration falling below the preselected concentration, an alarm such as a warning light 74 is actuated to warn the operator of a system abnormality. Typically, the concentration of peroxide in the aqueous solution is selected to be high enough that the selected hydrogen peroxide concentration level will always be maintained or exceeded, unless there is a defect in the aqueous hydrogen peroxide or the system. Optionally, a second source of higher concentration hydrogen peroxide solution can be connected with the vaporizer to boost the hydrogen peroxide concentration.

Optionally, an integrator 76 integrates the concentration of hydrogen peroxide over time. An end of cycle determining processor or means 78 receives the integrated concentration over time, the percent saturation, and the temperature in the chamber and determines when a preselected level of sterilization or high level disinfection assurance has been reached. Typically, at lower concentrations, the sterilization cycle is longer. At higher concentrations, the cycle is shortened. The end of cycle processor 78 is preferably a look-up table which has been preprogrammed based on iterative, trial and error calibration cycles. When the cycle is over, the end of cycle processor 78 causes the control valve controller 66 to close the control valve 12 and keep it closed.

Although described with reference to hydrogen peroxide, using other peracids and peroxy vapors, and mixtures of such vapors with each other and other compounds is also contemplated. Peracetic acid has been found to be a particularly effective antimicrobial either alone or in combination with hydrogen peroxide.

Although described in terms of a control system, it is to be appreciated that the same peroxide vapor concentration monitoring technique can also be used to measure concentrations of peroxide vapor for other reasons. For example, it can be used to measure the concentration of peroxide vapor in the ambient atmosphere of a facility in which peroxide is being used. The monitored concentration can be used to sound a warning in response to the monitored concentration of peroxide exceeding preselected safety limits for the personnel in the facility.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A peroxy vapor system including:
   a light source which supplies light with at least a component in the mid-infrared range;
   a detector which individually detects mid-infrared range light in (a) a first narrow mid-infrared spectrum absorbed by peroxy vapor and not absorbed by the carrier vapor, (b) a second narrow mid-infrared spectrum absorbed by a carrier vapor and not absorbed by the peroxy vapor, and (c) a third mid-infrared spectrum absorbed by neither the peroxy vapor nor the carrier vapor; and a processor for determining at least a concentration of the peroxy vapor from the detected light only in the mid-infrared range.

2. The system of claim 1 further including a source of hydrogen peroxide vapor and includes water vapor.

3. A peroxy vapor system including:
a light source which supplies light with at least a component in the mid-infrared range;
a detector which individually detects mid-infrared range light in (a) a first narrow spectrum which is centered at about 8,000 nanometers and is absorbed by peroxy vapor, (b) a second narrow spectrum absorbed by a carrier vapor, and (c) a third spectrum absorbed by neither the peroxy vapor nor the carrier vapor;
a processor for determining at least a concentration of the peroxy vapor from the detected light in the mid-infrared range.

4. The system as set forth in claim 1 wherein the concentration determining processor includes:
a means for determining at least one of (a) an absorbance of light in the first and second spectrums and (b) a transmittance of light in the first and second spectrums; and
a means for converting the determined absorbance or transmittance into a concentration of the peroxy vapor and a concentration of the carrier vapor.

5. The system as set forth in claim 1 further including:
a temperature sensor for sensing temperature; and
a percent saturation means for determining a percent saturation from the sensed temperature, the peroxy vapor concentration, and the carrier vapor concentration.

6. The system as set forth in claim 5 wherein the percent saturation means includes:
a means for converting concentrations of the peroxy vapor and the carrier vapor into partial vapor pressures;
a means for combining the partial vapor pressures; and
a means for converting the partial vapor pressure, the temperature, and the peroxy and carrier vapor concentrations into the percent saturation.

7. The system as set forth in claim 6 wherein at least one of the concentration determining processor, the vapor pressure determining means, and the saturation determining means includes a look-up table.

8. The system as set forth in claim 5 further including:
a source of a liquid peroxy and carrier mixture;
a vaporizer for vaporizing the liquid mixture to form the peroxy vapor and the carrier vapor;
a comparing means for comparing the determined percent saturation with a preselected percent saturation; and,
a control means for controlling vaporization of the liquid mixture in accordance with the comparison of the determined and preselected percent saturation.

9. The system as set forth in claim 8 wherein the control means is configured to control vaporization to maintain the percent saturation in a range of 95–99 percent saturation.

10. The system as set forth in claim 8 further including:
an integrating means for integrating the determined concentration of peroxy vapor over time; and,
an end of cycle means for terminating generation of the peroxy vapor in accordance with the integrated concentration over time.

11. The system as set forth in claim 5 further including:
a source of a liquid peroxy and carrier mixture; and,
a vaporizer for vaporizing the liquid mixture to form the peroxy vapor and the carrier vapor;

a control for controlling vaporization of the liquid mixture in accordance with at least one of the peroxy vapor concentration and the percent saturation.

12. A peroxy vapor system including:
a treatment region;
a means for generating peroxy vapor and supplying the peroxy vapor to the treatment region;
a light source which supplies light to the treatment region with at least a component in the mid-infrared range;
a detector which individually detects mid-infrared range light that has traversed at least a portion of the first treatment region in (a) a first narrow spectrum absorbed by peroxy vapor, (b) a second narrow spectrum absorbed by a carrier vapor, and (c) a third spectrum absorbed by neither the peroxy vapor nor the carrier vapor;
a processor for determining at least a concentration of the peroxy vapor from the detected light in the mid-infrared range;
an integrating means for integrating the determined concentration of peroxy vapor over time; and,
an end of cycle means for terminating generation of the peroxy vapor in accordance with the integrated concentration over time.

13. The system as set forth in claim 11, further including:
a comparing means for comparing the determined peroxy vapor concentration with a minimum peroxy vapor concentration.

14. A disinfection or sterilization system comprising:
a treatment chamber;
a source of aqueous peroxy solution;
a vaporizer for vaporizing the aqueous peroxy solution to form a peroxy vapor and a water vapor and for supplying the peroxy and water vapors to the treatment chamber;
a light source which projects a beam of light in a mid-infrared range through the peroxy and water vapors;
a mid-infrared light detector which detects (a) a first narrow spectrum absorbed by the peroxy vapor and not the water vapor, (b) a second narrow spectrum absorbed by the water vapor and not the peroxy vapor, and (c) a third spectrum absorbed by neither the peroxy nor the water vapor;
an absorbance/transmittance processor which converts the detected first, second, and third spectrum light into one of (a) absorbance values indicative of mid infrared light absorbed by the peroxy and water vapors and (b) transmittance values indicative of mid-infrared light transmitted through the peroxy and water vapors;
a processor which converts the determined absorbance/transmittance values into a concentration of the peroxy vapor and a concentration of the water vapor;
a temperature monitor for monitoring temperature in the treatment chamber;
a percent saturation processor which converts the concentration of the peroxy vapor, the concentration of the water vapor, and the temperature into an indication of a percent saturation in the treatment chamber; and,
a control processor which controls the generation of peroxy and water vapor in accordance with the determined percent saturation.

15. The system as set forth in claim 14 wherein the saturation processor includes:
a means for determining partial vapor pressures of the peroxy vapor and the water vapor from the determined peroxy vapor concentration and the determined water vapor concentration;

a means for combining the partial vapor pressures to form a total vapor pressure; and a look-up table for determining the percent saturation from the monitored temperature, the peroxy and water vapor concentrations, and the total vapor pressure.

16. The system as set forth in claim 14 wherein the control processor includes:
    a means for comparing the determined percent saturation with a preselected percent saturation; and
    a means for controlling the generation of peroxy and water vapor in accordance with the percent saturation comparison.

17. The system as set forth in claim 16 wherein the control processor further includes:
    an integrator for integrating the concentration of peroxy vapor over time; and,
    a means for ending disinfection or sterilization cycle in accordance with the integrated concentration of peroxy vapor.

18. The system as set forth in claim 14 wherein the peroxy vapor includes hydrogen peroxide vapor.

19. A peroxy vapor method including:
    projecting light in a mid-infrared range through a monitored region;
    detecting mid-infrared light in (a) a first narrow spectrum absorbed by the peroxy vapor, (b) a second narrow spectrum absorbed by a carrier vapor, and (c) a third spectrum absorbed by neither the peroxy vapor nor the carrier vapor; and,
    determining at least a concentration of the peroxy vapor from the light detected in the mid-infrared range.

20. The method as set forth in claim 19 wherein the peroxy vapor includes hydrogen peroxide and the carrier vapor includes water vapor.

21. The method as set forth in claim 19 wherein the first narrow spectrum is centered about 8,000 nanometers.

22. The method as set forth in claim 19 further including:
    converting the determined spectrums into one of absorbance and transmittance of mid infrared light through the peroxy vapor and the carrier vapor and converting the determined one of the absorbance and transmittance into the concentration of the peroxy vapor and a concentration of the carrier vapor.

23. The method as set forth in claim 19 further including:
    sensing a temperature in the monitored region; and
    determining a percent saturation of vapor in the monitored region from the sensed temperature and the peroxy concentration and a carrier vapor concentration.

24. The method as set forth in claim 23 wherein the step of determining the percent saturation further includes:
    converting the concentrations of the peroxy vapor and the carrier vapor into partial vapor pressures of the peroxy and carrier vapors;
    combining the partial vapor pressures; and,
    determining the percent saturation from the monitored temperature and the total vapor pressure.

25. The method as set forth in claim 23 further including:
    supplying peroxy and carrier vapor to the monitored region; and,
    controlling the supplying of peroxy and carrier gas vapor in accordance with the determined percent saturation.

26. The method as set forth in claim 25 wherein the supply of peroxy and carrier vapor is controlled to maintain the peroxy and carrier gas vapor in the monitored region between 95–99% of saturation.

27. The method as set forth in claim 25 further including:
    integrating the determined peroxy vapor concentration with time; and
    terminating supplying the peroxy and carrier vapor to the monitored region in accordance with the integrated concentration.

28. The method as set forth in claim 20 wherein the first spectrum is absorbed by the hydrogen peroxide vapor and is not absorbed by the water vapor and the second spectrum is absorbed by the water vapor and not by the hydrogen vapor.

* * * * *